United States Patent [19]

DuBose

[11] Patent Number: 4,850,997

[45] Date of Patent: Jul. 25, 1989

[54] SPRAY VACCINATOR APPARATUS

[75] Inventor: Ronald A. DuBose, Smyrna, Ga.

[73] Assignee: Keevet Laboratories, Inc., Anniston, Ala.

[21] Appl. No.: 6,570

[22] Filed: Jan. 23, 1987

[51] Int. Cl.$^4$ .............................................. A61M 35/00

[52] U.S. Cl. ..................................... 604/289; 119/160

[58] Field of Search ................ 604/289, 290; 119/159, 119/160, 1

[56] References Cited

U.S. PATENT DOCUMENTS

| | | | |
|---|---|---|---|
| 4,316,464 | 2/1982 | Peterson . | |
| 4,449,968 | 5/1984 | Peterson | 604/290 |
| 4,551,139 | 11/1985 | Plaas et al. | 604/289 |
| 4,674,490 | 6/1987 | Frankel et al. | 119/160 |
| 4,679,551 | 7/1987 | Anthony | 604/289 |

*Primary Examiner*—C. Fred Rosenbaum
*Assistant Examiner*—Gene B. Kartchner
*Attorney, Agent, or Firm*—Jones, Askew & Lunsford

[57] ABSTRACT

A spray vaccination apparatus using a positive-displacement peristaltic pump to deliver vaccinating liquid to the spray nozzles. The vaccinating liquid is contained in a plastic bag similar to an IV bag, and a flexible plastic tube extends from the bag to the spray nozzles. A peristaltic pump engages this tube for positive-displacement pumping. The pump is actuated for a predetermined increment of time, whenever a tray of baby chicks is inserted into the spray vaccination apparatus, thereby spraying the chicks with vaccinating liquid for a predetermined interval. The spray nozzles preferably are equipped with valves which open only while the pump operates, providing a relatively abrupt onset and termination of spray. All elements of the liquid delivery system remain closed and sealed from the atmosphere, thereby maintaining a sterile condition throughout. These components preferably are disposable, eliminating the need to cleanse the system components periodically.

7 Claims, 1 Drawing Sheet

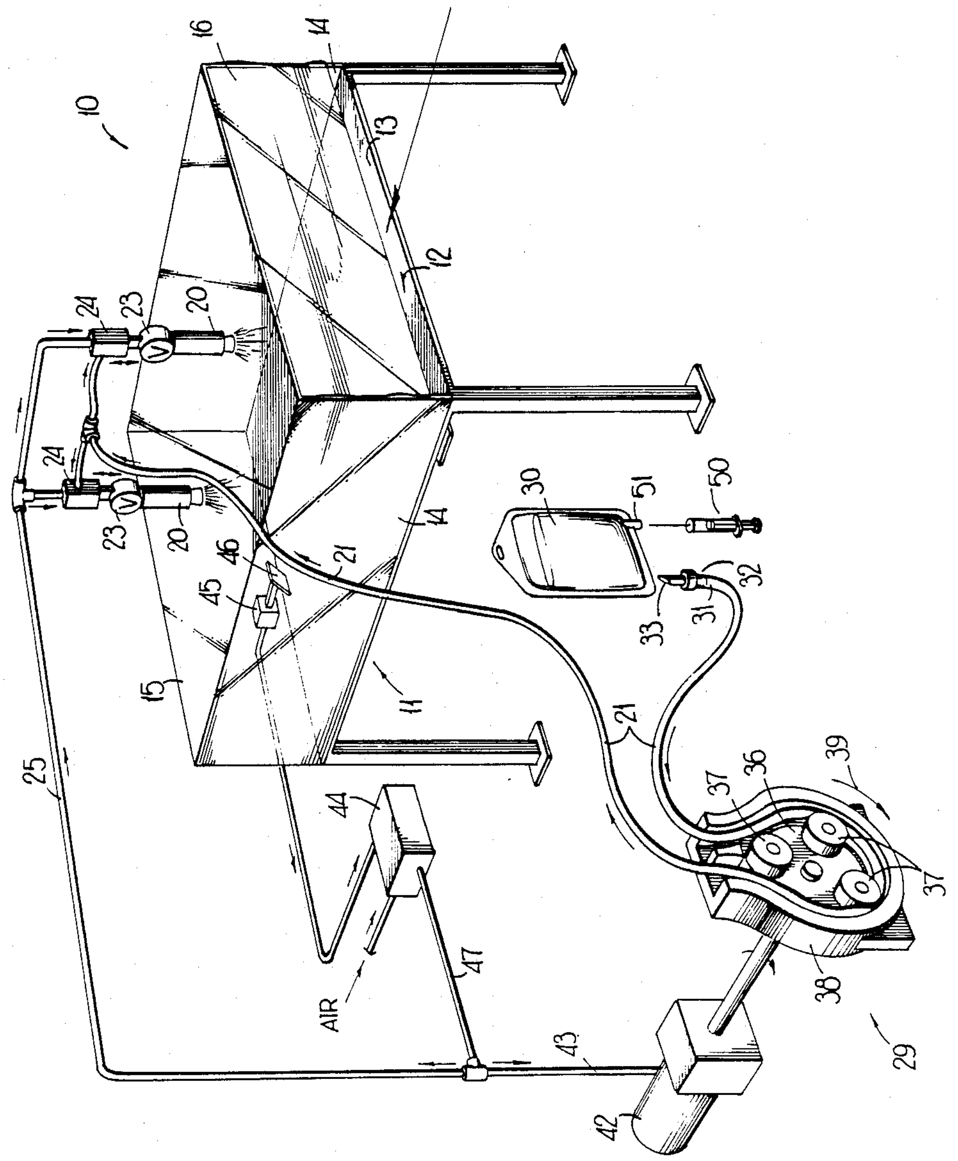
10
16
14
13
12
11
15
14
20
23
24
21
45
46
30
51
50
32
31
33
25
44
47
AIR
43
42
29
38
37
36
39

SPRAY VACCINATOR APPARATUS

Field of the Invention

This invention relates in general to spray vaccinators, and relates in particular to spray vaccination apparatus used to vaccinate baby chicks and other fowl.

Background of the Invention

Baby chickens and other fowl, when raised commercially, typically are vaccinated to prevent infectious diseases which otherwise could rapidly propagate to infect all birds housed together. Vaccination of chicks on a commercial scale presently is accomplished either by subcutaneous injection, where each individual chick is individually injected with vaccine, or by spray vaccination. In the latter technique, chicks are sprayed with a solution containing the desired vaccine. The spray enters the body of each chick through its mucous membrane, typically at the eyes or nostrils of the chick, and thereby accomplishes the desired vaccination.

Spray vaccination offers the practical advantage that many chicks at a time can be sprayed, so that each individual chick need not be handled as is required with subcutaneous injection. In the typical spray vaccination procedure, a tray containing a number of chicks is inserted in a housing equipped with spray nozzles. The spray nozzles are connected to a liquid tank containing a supply of the vaccine mixed in an appropriate diluent, and the tank is pressurized with compressed air. A valve is located at each spray nozzle, and these valves are selectively opened by air-powered operators. When the tray containing the chicks is fully introduced into the spray region, a control mechanism momentarily actuates the valve operators to open the valves, allowing air pressure in the tank to force the vaccine-containing liquid through the nozzles, thereby spraying the chicks. The valve operating mechanism is timed so that the valves automatically close after a predetermined interval. The tray containing the chicks then is removed from the housing, and the apparatus is ready to vaccinate another batch of chicks.

Maintaining the sterility of the vaccinating liquid delivery system presents a problem with existing spray vaccinator apparatus. The vaccine typically is available, in freeze-dried form and is mixed with a sterile diluent shortly before use. This mixture is placed in the supply tank, which is then pressurized as mentioned above to force the liquid to the spray nozzles whenever the nozzle valves are opened. Because the vaccine-diluent mixture has a relatively short lifetime measured in hours, the tank must necessarily be opened and closed a number of times during the daily operation of the spray vaccinator. This repeated opening of the vaccine tank takes place in an unsterile environment. Furthermore, the compressed air supplied to pressurize the tank is compressed ambient air, subject to chemical or biological contamination present in the air itself or within the air compressor and supply lines furnishing compressed air to the vaccine tank. The positive pressure maintained in the tank forces this airborne contamination into the vaccinating liquid.

Other problems also arise from the need to maintain sterility in the liquid supply system of art spray vaccinators. After each daily use of such vaccinators, the liquid supply system must be cleansed. This usually is accomplished by running clear water through the system to flush the vaccine from the supply tank, the liquid line running to the spray nozzles, and the spray nozzles themselves. A disinfectant solution then is placed in the liquid supply tank, and this solution is forced through the system including the supply line and spray nozzles. The disinfectant solution remains in the liquid system overnight, to prevent the onset of any biological contamination. Before vaccinating any chicks the following morning, the preceding cleanup steps must be accomplished in reverse, first flushing out the disinfectant from the liquid system, and then flowing some vaccine through the system to purge all traces of the disinfectant before vaccinating the first batch of chicks. These cleanup and reservecleanup steps waste operator time, and the reverse-cleanup step also wastes vaccine.

Objects of the Invention

Accordingly, it is an object of the present invention to provide improved spray vaccination apparatus.

It is another object of the present invention to provide spray vaccination apparatus having reduced susceptibility to contamination during operation.

It is a further object of the present invention to provide a spray vaccination apparatus having a vaccine supply system that remains closed to maintain sterile conditions during operation.

It is a further object of the present invention to provide spray vaccination apparatus capable of using relatively inexpensive disposable components throughout the vaccine supply system.

Other objects and advantages of the present invention will become more readily apparent from the following.

Summary of Invention

Stated in general terms, the fluid vaccinating apparatus of the present invention includes a vaccine supply system that is closed and sealed from the source of vaccine to the spray nozzles. This vaccine supply system includes a nonwettable pump which positively displaces liquid from the supply to the nozzles, eliminating compressed air as a source of chemical or biological contamination. The liquid pump operates only while spraying each individual batch of chicks.

Stated in somewhat greater detail, the spray vaccinator apparatus of the present invention includes a peristaltic pump for positive displacement of vaccinating liquid from the liquid supply to the spray nozzles. This pump preferably is started when the tray or other carrier containing chicks is fully inserted in the spray apparatus, and is automatically stopped after a short predetermined time necessary to accomplish the desired spraying. The spray nozzles preferably are equipped with valves synchronized to open and close concurrently with the operation of the peristaltic pump, providing a relatively abrupt onset and termination of liquid spray from the nozzles.

The liquid spray of vaccine in the present invention preferably is a disposable plastic bag like an intravenous (IV) bag in common medical usage. These bags are supplied containing a quantity of sterile diluent, and the vaccine solution is prepared and then injected into the bag shortly before use. The bag is connected to a disposable flexible tubing which passes through the peristaltic pump and leads to the spray nozzles. The plastic tubing and spray nozzles themselves preferably are inexpensive and disposable, so that these disposable elements (along with expended bags) can be discarded at the end of each day at less cost than presently is incurred in cleaning and reverse-cleaning conventional spray vaccinator apparatus.

Further details of the present invention may be seen from the following description of a preferred embodiment.

The Figure

The FIGURE is a pictorial view showing a fluid vaccination apparatus equipped according to an embodiment of the present invention.

Description of Preferred Embodiment

The FIGURE includes a spray vaccinator apparatus shown generally at 10 and including a table 11 configured to receive a tray of baby chicks. By way of example, a typical tray can contain approximately 100 baby chicks for vaccination. One end 12 of the table is open to receive an individual tray (not shown), on the floor 13 of the table. The sides 14 and the end 15 of the table, extending upwardly from the floor 13, preferably are transparent and made of a material such as clear plastic, so that the baby chicks are not startled by being introduced to a darkened enclosure. A curtain 16 of clear plastic material at least partially covers the open end 12 of the table, permitting easy insertion and withdrawal of trays containing chicks.

Mounted a distance above the floor 13 of the table 11 are the spray nozzles 20. These nozzles direct an atomized spray of vaccination liquid downwardly toward a tray inserted through the opening 12 into the table. Two spray nozzles 20 are shown in the disclosed embodiment, although it should be understood that a greater or lesser number of spray nozzles may accomplish complete spray coverage of the chicks in the tray. The spray nozzles 20 are connected to the liquid supply line 21, through which is pumped the liquid containing the appropriate vaccine. Each spray nozzle 20 preferably is equipped with a normally closed valve 23 which prevents the outflow of liquid through the spray nozzles. The purpose of these nozzle valves 23 is described below. Each normally-closed valve 23 is operated by an actuator 24, which selectively opens the nozzle valves in unison. The valve actuators 24 are airpowered, and operator to open the nozzle valves 23 whenever air pressure is applied on the valve control line 25.

The liquid supply line 21 extends upstream from the spray nozzles 20 and passes through a peristaltic pump 29, and thence continues upstream from the pump 29 to connect with the bag 30 containing the vaccination solution. The bag 30 preferably is similar in nature and construction to the conventional IV bag used for dispensing fluids to human patients. This bag 30 contains the mixture of diluent and vaccine which is sprayed onto the chicks with the present apparatus.

The inlet end 31 of the liquid supply line 20 preferably is attached to the bag 30 by means of the stab 32. The stab functions like a union, interconnecting the end 31 with the bag, and includes a beveled end 33 sharpened to penetrate a mating portion of the bag 30 and to maintain a liquid-tight seal with the bag. The supply line 21 is a flexible plastic tubing suitable for use with a peristaltic pump.

The peristaltic pump 29 includes a rotor 36 peripherally mounting a number of rollers 37 which nearly contact the curved compression surface 38 of the pump as the rotor turns. The liquid supply line 21 lies within the compression surface 38, and at least two rollers 37 pinch shut a section of the liquid supply line at any position of the rotor. Thus, as the rotor turns in the clockwise direction indicated by the arrow 39, liquid in the supply line 21 is positively displaced by the peristaltic pump in a direction flowing toward the spray nozzles 20 on the table 11.

The rotor 36 of the peristaltic pump 29 is mechanically driven by the air motor 42, which is adjustable to vary the pump speed for a given air pressure input to the motor along the line 43. This line 43 is connected to the output of a timer valve 44, operated in response to the lever-actuated pneumatic control 45. The control 45 includes the actuating lever 46, positioned in the table 11 for actuation whenever a chick tray is fully inserted on the table. The timer valve 44 responds to each actuation of the control 45 to open for a predetermined time, and then closes and resets itself for the next actuation of the control 45. Timer valves functioning in this manner are known to those skilled in the art and need not be described further herein.

The timer valve 44 is connected to an air supply line 48, and delivers the timed flows of air along the outlet line 47, which connects to the line 43 to operate the air motor 42. The outlet line 47 also supplies air to the valve control line 25 and the valve actuators 24 which operate the valves 23 associated with the spray nozzles 20.

The operation of the disclosed spray vaccinator apparatus is now discussed. Bags 30 are supplied filled with sterile diluent, and the freeze-dried vaccine itself is mixed with a quantity of diluent shortly before its intended use. This mixed vaccine in concentrated form is injected into the diluent within the bag 30 by means of the hypodermic syringe 50. The bag 30 is provided with a injectable membrane or septum 51 which allows penetration by the syringe 50 and then reseals after the syringe is withdrawn. The vaccine thus is introduced under sterile conditions into the diluent within the bag 30.

The stab 32 next is attached to the bag 30 in the manner previously described. This connection allows the diluent to flow from the bag 30 through the liquid supply line 21 as the peristaltic pump 29 is operated to purge air from the liquid supply line leading to the spray nozzles 20. At this point, the apparatus 20 is ready to being spray vaccinations.

As previously mentioned, a tray containing baby chicks is inserted in the table 11 through the opening 12. As the tray is fully inserted, the tray contacts the actuator lever 46 of the control 45, which operates the timer valve 44 to supply air pressure on the outlet line 47 for a predetermined time. This air pressure on the line 47 actuates the air motor 42 to operate the peristaltic pump 29 for the predetermined time, and simultaneously operates the valve actuators 24 to open the nozzle valves 23 for that time. Consequently, the peristaltic pump 29 delivers a positive displacement of liquid from the bag 30 to the spray nozzles 20, which spray the vaccine onto the chicks in the tray. This spray continues only for the duration determined by the timer valve 44, as the peristaltic pump stops operating and the nozzle valves 23 close when the timer valve shuts off air to the outlet line 47. The operator now withdraws the tray of chicks from the table 11 and inserts a new tray; the spray cycle recurs every time the control 45 is actuated by a new tray of chicks.

The combination of the positive-displacement pump 29 and the nozzle valves 23 provides a relatively abrupt commencement and interruption of liquid spray from the nozzles, a desirable feature which eliminates or reduces dripping and inadequate atomization of liquid at the beginning and end of each spray cycle. This relatively abrupt spraying action occurs because some liquid pressure remains in the liquid supply line 21 extending from the peristaltic pump 29 to the nozzle valves 23, whenever the nozzle valves close at the end of a spray cycle. The pump rollers 37, which compress the flexible liquid supply line completely closed within the pump, prevent this pressure from bleeding back into the bag 30, at least for the relatively short time between successive operations of the apparatus. Thus, as the next tray of chicks trips the actuator lever 46 to open the nozzle valves 23, the retained liquid pressure in the liquid supply line 21 immediately commences the liquid spray from the nozzles 20, although the peristaltic pump 29 requires some brief finite time to reach operating speed. This flow through the nozzles is abruptly terminated when the nozzle valves 23 close at the end of the next spray cycle.

It is contemplated that every element of the vaccine dispensing system in the disclosed apparatus preferably is disposable. No part of the peristaltic pump 29 contacts the pumped liquid and, of course, this pump is not a disposable item. However, the individual bags 30, the stab 32, the liquid supply line 21, and the spray nozzles themselves all preferably are made of relatively inexpensive materials and are intended for disposal at the end of an operating day or some other suitable interval. A number of bags 30 containing the vaccine will be used during the course of each day, and a fresh bag is attached as needed by withdrawing the stab 32 from a depleted bag and inserting the stab into the fresh bag of vaccine. The other disposable components can be prepackaged in sterile form, preferably by known gas sterilizing techniques. The spray nozzles 20, for example, can be adapted from nozzles of the kind associated with aerosol spray cans, as such nozzles already contain a normally-closed valve mechanism and are mass-produced at a cost low enough for daily disposal.

It should be understood that the foregoing refers only to a disclosed embodiment of the present invention, and that numerous changes and modifications can be made therein without departing from the spirit and scope of the invention as defined in the following claims.

I claim:

1. Apparatus for spray vaccinating living organisms, comprising:

housing means defining a spray region for receiving a carrier containing organisms to undergo spray vaccination;

spray nozzle disposed to dispense a liquid spray in said spray region;

an aseptic supply of liquid containing vaccine;

a sterile fluid conduit extending between said vaccine supply and said spray nozzle;

nonwettable pump means operatively associated with said conduit to displace liquid through the conduit from said vaccine supply to said spray nozzle;

said spray nozzle being selectively operative to dispense the liquid spray in response to the liquid displacement through the conduit; and control means responsive to the placement of a carrier in said spray region and operative to actuate said pump means for a predetermined interval, so that an amount of the vaccine fluid is sprayed on the organisms without exposure to possible contamination in the pump means.

2. Apparatus as in claim 1, further comprising:

valve means associated with said spray nozzle; and said valve means being selectively operative in response to said control means to permit the flow of pumped liquid through said spray nozzle only while said pump means is actuated, thereby providing an abrupt onset and termination of liquid spray in the spray region.

3. Apparatus as in claim 1, wherein:

said conduit comprises flexible tubing; and said pump means comprises a peristaltic pump operatively associated with said flexible tubing to positively displace liquid through the tube to the spray nozzle, in response to said control means.

4. Apparatus as in claim 3, wherein:

valve means associated with said spray nozzle and normally blocking liquid flow through the nozzle; and means operative in response to said control means to unblock said valve means only while said peristaltic pump operates, so that a positive liquid pressure remains in the flexible tubing between the peristaltic pump when inoperative and the valve means when closed, thereby providing an abrupt onset of liquid spray at said spray nozzle when the valve means is next opened.

5. Apparatus for spray vaccinating living organisms, comprising:

housing means defining a spray region for receiving a carrier containing organisms to undergo spray vaccination;

a disposable sealed container for containing vaccine and operative to reseal itself during and after puncture by relatively sharp objects;

a disposable sterile fluid conduit having a means at one end for puncturing said container;

a nonwettable pump means operatively associated with said conduit to positively displace fluid from said container and to produce pressure in said conduit downstream from the pump;

a disposable spray means connected to the other end of the sterile fluid conduit and selectively operative to dispense an aerosol spray in said spray region in response to the pressure generated by said nonwettable pump; and control means responsive to the placement of a carrier in said spray region and operative to actuate said pump means for a predetermined interval;

whereby economical sterile operation is achieved by replacing said container, said conduit, and said spray means on a daily basis.

6. Apparatus as in claim 5, further comprising:

valve means associated with said spray means;

said valve means being selectively operative in response to said control means to permit the flow of pumped fluid through said spray means only while said pump means is actuated; and said valve means being further selectively operative in response to said control means to stop the flow of pumped fluid so that a pressure head is maintained downstream of said pump means for a duration of time after said pump means is stopped;

thereby providing an abrupt onset and termination of fluid spray in the spray region.

7. Apparatus as in claim 5, wherein:

said conduit comprises flexible tubing; and said pump means comprises a peristaltic pump operatively associated with said flexible tubing to positively displace fluid through the tube to the spray means, in response to said control means.

* * * * *